United States Patent
Byrnes et al.

(10) Patent No.: US 11,335,435 B2
(45) Date of Patent: *May 17, 2022

(54) IDENTIFYING ANCESTRAL RELATIONSHIPS USING A CONTINUOUS STREAM OF INPUT

(71) Applicant: Ancestry.com DNA, LLC, Lehi, UT (US)

(72) Inventors: Jake Kelly Byrnes, San Francisco, CA (US); Aaron Ling, Belmont, CA (US); Keith D. Noto, San Francisco, CA (US); Jeremy Pollack, San Francisco, CA (US); Catherine Ann Ball, San Francisco, CA (US); Kenneth Gregory Chahine, Park City, UT (US)

(73) Assignee: Ancestry.com DNA, LLC, Lehi, UT (US)

( * ) Notice: Subject to any disclaimer, the term of this patent is extended or adjusted under 35 U.S.C. 154(b) by 858 days.

This patent is subject to a terminal disclaimer.

(21) Appl. No.: 16/152,169

(22) Filed: Oct. 4, 2018

(65) Prior Publication Data

US 2019/0139624 A1 May 9, 2019

Related U.S. Application Data

(63) Continuation of application No. 14/029,765, filed on Sep. 17, 2013, now Pat. No. 10,114,922.

(60) Provisional application No. 61/874,329, filed on Sep. 5, 2013, provisional application No. 61/702,160, filed on Sep. 17, 2012.

(51) Int. Cl.
| | | |
|---|---|---|
| *G16B 20/20* | (2019.01) | |
| *G16B 20/00* | (2019.01) | |
| *G16B 50/30* | (2019.01) | |
| *G16B 50/00* | (2019.01) | |
| *G16B 20/40* | (2019.01) | |

(52) U.S. Cl.
CPC .............. *G16B 20/20* (2019.02); *G16B 20/00* (2019.02); *G16B 50/30* (2019.02); *G16B 20/40* (2019.02); *G16B 50/00* (2019.02)

(58) Field of Classification Search
CPC .. G06F 16/285; G06F 16/9535; G06F 16/951; G06F 16/24578; G06F 16/2282; G06F 16/00; G06F 16/24575; G06F 16/955; G06F 16/2255; G06F 16/2272; G06F 16/2228; G06F 16/26; G06F 16/20; G06F 16/21; G06F 16/22; G06F 16/221; G06F 16/211; G06F 17/10; G06F 17/15; G06F 17/11; G06F 17/16; G06F 17/18; G06F 17/40; G06F 16/283; G06F 16/245; G06F 16/9024; G06F 16/284; G06F 16/2457; G06F 30/20; G16B 20/00; G16B 20/20; G16B 20/40; G16B 30/00; G16B 30/10; G16B 50/00; G16B 40/00; G16B 20/10; G16B 30/20; G16B 45/00; G16B 50/10; G16B 50/30; G16B 10/00; G16B 5/00; G16B 50/20; G16B 5/20; G16H 50/30; G16H 50/70; G16H 10/60; G16H 10/20; G16H 10/40; G16H 15/00; G06N 7/005; G06N 5/022; G06N 5/003; G06N 5/02
See application file for complete search history.

(56) References Cited

U.S. PATENT DOCUMENTS

| | | | |
|---|---|---|---|
| 10,114,922 B2 * | 10/2018 | Byrnes | G16B 50/30 |
| 2010/0169338 A1 | 7/2010 | Kenedy et al. | |
| 2015/0363481 A1 | 12/2015 | Haynes | |

OTHER PUBLICATIONS

Purcell et al. Am J Hum Genetics vol. 81, pp. 559-575 (2007).
"What is persistence and why does it matter, 2010 DataStax" http://www.datastax.com/dev/blog/whatpersistenceandwhydoesitmatter Matt Pfeil Oct. 22, 2010; downloaded Mar. 22, 2016.
Gusev, A. "Germline," Columbia.edu, Last Change Log Jul. 3, 2012, 4 pages, [Online] [Retrieved on Jun. 24, 2015] Retrieved from the Internet<URL: http://www1.cs.columbia.edu/.about.gusev/germline/>.
Gusev, A. et al., "Whole Population, Genomewide Mapping of Hidden Relatedness," Genome Research, Feb. 2009, 39 pages, vol. 19, No. 2.
United States Office Action, U.S. Appl. No. 14/029,765, filed Jan. 25, 2018, 14 pages.
United States Office Action, U.S. Appl. No. 14/029,765, filed May 8, 2017, 12 pages.
United States Office Action, U.S. Appl. No. 14/029,765, filed Nov. 21, 2016, 12 pages.
United States Office Action, U.S. Appl. No. 14/029,765, filed Mar. 30, 2016, 18 pages.

* cited by examiner

*Primary Examiner* — Mary K Zeman
(74) *Attorney, Agent, or Firm* — Fenwick & West LLP

(57) ABSTRACT

Identification of inheritance-by-descent haplotype matches between individuals is described. A set of tables including word match, haplotypes and segment match tables are populated. DNA samples are received and stored. A word identification module extracts haplotype values from each sample. The word match table is indexed according to the unique combination of position and haplotype. Each column represents a different sample, and each cell indicates whether that sample includes that haplotype at that position. The haplotypes table includes the raw haplotype data for each sample. The segment match table is indexed by sample identifier, and columns represent other samples. Each cell is populated to indicate for each identified sample pair which position range(s) include matching haplotypes for both samples. The tables are persistently stored in databases of the matching system. As new sample data is received, each table is updated to include the newly received samples, and additional matching takes place.

20 Claims, 7 Drawing Sheets

Specification includes a Sequence Listing.

Word_Match_Table

| Word haplotype key | Users |
|---|---|
| chr1 00000000000000 ACTACGACCA | $U_1, ..., U_7$ |
| chr1 00000000000000 ACTACGACTC | $U_1, ..., U_3$ |
| chr1 00000000000010 TCGCCTTAGC | $U_3, ..., U_8$ |
| chr3 00000000000040 TTCGCTAACA | $U_2, ..., U_5$ |
| ... | ... |

Haplotypes Table

| Chr_User key | User_Position Matches | | |
|---|---|---|---|
| | 000_Odd | 000_Even | 010_Odd |
| Chr1_U₁ | ACTACGACCA | ACTACGACTC | TCGCCTGAGA |
| Chr1_U₂ | ACTACGACCA | ACTACGACTC | TCGCCTGAGA |
| Chr1_U₃ | ACTACGACCC | ACTACGACTC | TCGCCTTAGC |

Segment_Match Table 402

| Chr_User key | User_Position Matches | | |
|---|---|---|---|
| | $U_1$ | $U_2$ | $U_3$ |
| Chr1_$U_1$ | N/A | 10-40,...,550-700 | ... |
| Chr1_$U_2$ | 10-40,...,550-700 | N/A | ... |
| Chr1_$U_3$ | 0-10,...,610-860 | 100-400,...,500-700 | ... |
| ... | | | |

FIG. 4

IDENTIFYING ANCESTRAL RELATIONSHIPS USING A CONTINUOUS STREAM OF INPUT

RELATED APPLICATIONS

This application is a continuation of U.S. patent application Ser. No. 14/029,765, filed on Sep. 17, 2013, which claims the benefit of U.S. Provisional applications 61/702,160 filed on Sep. 17, 2012 and 61/874,329 filed on Sep. 5, 2013, all of which are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Oct. 16, 2013, is named 41690US_CRF_sequencelisting.txt and is 1,462 bytes in size.

BACKGROUND

Field

The disclosed embodiments relate to identifying individuals in an existing dataset of genetic information that are related to individuals whose genetic information is newly analyzed.

Description of Related Art

Although humans are, genetically speaking, almost entirely identical, small differences in our DNA are responsible for much of the variation between individuals. Stretches of DNA that are determined to be relevant for some purpose are referred to as haplotypes. Haplotypes are identified based on consecutive single nucleotide polymorphisms (SNPs) of varying length. Certain haplotypes shared by individuals suggests a familial relationship between those individuals based on a principal known as identity-by-descent (IBD).

Because identifying segments of IBD DNA between pairs of genotyped individuals is useful in many applications, numerous methods have been developed to perform IBD analysis (Purcell et al. 2007, Gusev et al. 2009, Browning and Browning 2011, Browning and Browning 2013). However, these approaches do not scale for continuously growing very large datasets. For example, the existing GERMLINE implementation is designed to take a single input file containing all individuals to be compared against one another. While appropriate for the case in which all samples are genotyped and analyzed simultaneously, this approach is not practical when samples are collected incrementally.

SUMMARY

Described embodiments enable identification of IBD and consequently familial relationships within received samples and between a received sample and samples in an existing data set. An initial configuration includes populating a set of tables including a word match table, a haplotypes table and a segment match table. A set of phased DNA samples are received, e.g., from a DNA service, and stored in a DNA database. A word identification module extracts haplotype values from each sample. The word match table is indexed in one embodiment according to haplotypes, for example a specific haplotype on a specific chromosome. Each column of the word match table represents a different sample, and each cell includes an indication of whether that sample includes that haplotype at that position. The haplotypes table is populated to include the raw haplotype data for each sample. The segment match table is indexed by sample identifier, and columns represent other samples. Each cell of the table is populated to indicate for each identified sample pair which position range(s) include matching haplotypes for both samples.

The tables are persistently stored in databases of the matching system. Subsequently, as new sample data is received, each of the tables is updated to include the newly received samples, and additional matching takes place. The persistence of the tables avoids the necessity of recomputing relationships with the addition of each new sample, thus allowing for rapid and efficient scaling of the identification system and accommodation of continuous or periodic input of new sample data.

BRIEF DESCRIPTION OF THE DRAWINGS

FIG. 2 illustrates an example of a word match table according to one embodiment. FIG. 2 discloses SEQ ID NOS 2-5, respectively, in order of appearance.

FIG. 3 illustrates an example of a haplotype table in accordance with one embodiment. FIG. 3 discloses SEQ ID NOS 2-3, 6, 2-3, 6-7 and 3-4, respectively, in order of appearance.

FIG. 4 illustrates an example of a segment match table in accordance with one embodiment.

DETAILED DESCRIPTION

Figure 1:
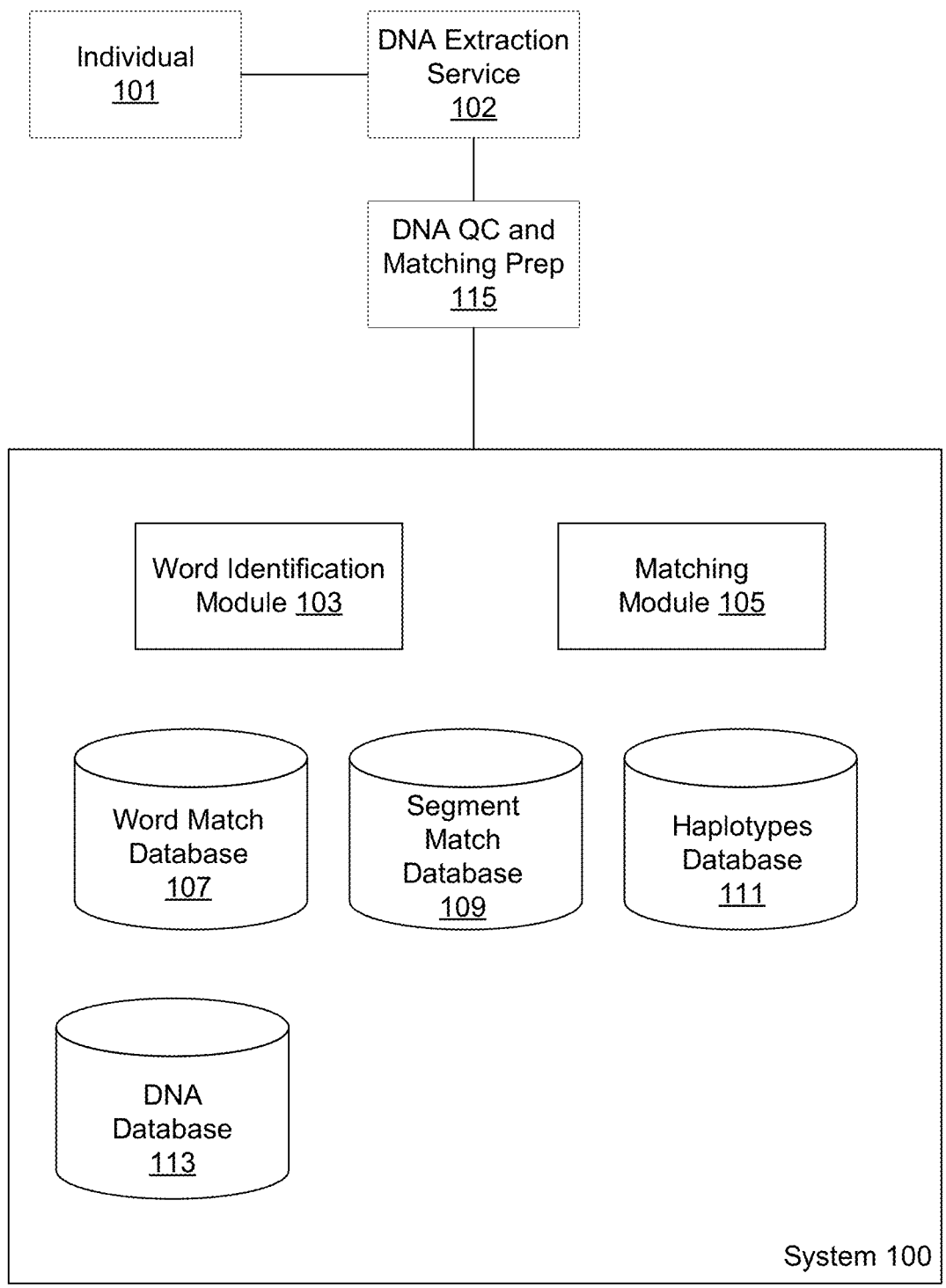
FIG. 1 is a block diagram of a system architecture and environment in accordance with one embodiment.

FIG. 1 is a block diagram of the architecture and environment of system 100 according to one embodiment. System 100 includes a word identification module 103, a word match database 107, a segment match database 109, a haplotype database 111, and a DNA database 113. Also depicted in FIG. 1 are individual 101 (i.e. a human or other organism), DNA extraction service 102, and a DNA quality control (QC) and matching preparation service 115. Each of these illustrated features is described further below. Note that for purposes of clarity, only one of each item is included in the figure, but when implemented multiple instances of any or all of the depicted modules may be employed, as will be appreciated by those of skill in the art.

System 100 may be implemented in hardware or a combination of hardware and software. For example, system 100 may be implemented by one or more computers having one or more processors executing application code to perform the steps described here, and data may be stored on any conventional storage medium and, where appropriate, include a conventional database server implementation. For purposes of clarity and because they are well known to those of skill in the art, various components of a computer system, for example, processors, memory, input devices, network devices and the like are not shown in FIG. 1. In some embodiments, a distributed computing architecture is used to implement the described features. One example of such a distributed computing platform is the Apache Hadoop project available from the Apache Software Foundation.

Individuals 101 provide DNA samples for analysis of their genetic data. In one embodiment, an individual uses a sample collection kit to provide a sample, e.g., saliva, from which genetic data can be reliably extracted according to conventional methods. DNA extraction service 102 receives the sample and genotypes the genetic data, for example by extracting the DNA from the sample and identifying values of single nucleotide polymorphisms (SNPs) present within the DNA. DNA QC and matching preparation service 115 phases the genetic data and assesses data quality by checking various attributes such as genotyping call rate, genotyping heterozygosity rate, and agreement between genetic and self-reported gender. System 100 receives the genetic data from DNA extraction service 102 and stores the genetic data in DNA database 113.

Initial Configuration

For ease of explanation, we assume an initial set of DNA samples have been collected and are stored in DNA database 113. A decision for the implementer is to select a segment or window length to be used by system 100. In practice, window sizes of 100 or more SNPs are appropriate, but for purposes of illustration here we assume without loss of generality a window size of 10 SNP markers. The value of each marker will be one of two genetic bases, and each individual is associated with two sequences of values called haplotypes, because each person has two copies of each chromosome. For example, the genetic data for individual 1, haplotype 1, markers 1 through 10 might be: GCCATATGGC (SEQ ID NO: 1).

In processing the initial samples, word identification module 103 and matching module 105 populate an initial set of tables that we refer to below as the word match table, haplotypes table and segment match table. In the illustrated embodiment, the word match table is stored in word match database 107; the haplotypes table is stored in haplotype database 111; and the segment match table is stored in segment match database 109.

FIG. 2 illustrates a word match table 202 according to one embodiment. Word identification module 103 obtains genetic data for an individual from DNA database 113 and uses the data to populate the table. In one embodiment, each row of word match table 202 specifies a haplotype observed in a particular genomic window, and each column specifies an individual (referred to interchangeably as a user). A table cell (i.e. a particular row/column combination) therefore indicates whether that user has that haplotype, and reading across a row enables identification of all such users with the haplotype. In various embodiments, the haplotypes are hashed prior to insertion into the table 202. Depending on the window size and number of samples, this table may be very large. However, it is also very sparse as each individual has at most two distinct haplotypes for each window. Distributed, scalable big data stores such as Apache HBase are particularly well suited to storing and querying very large, very sparse tables such as this. In one embodiment, the row keys for word match table 202 are of the form [CHROMOSOME] [POSITION] [HAPLOTYPE], where [CHROMSOME] and [POSITION] denote the unique genomic location of the first SNP in a particular window and [HAPLOTYPE] is the sequence of bases observed in this window.

For example, referring still to FIG. 2, a row key of the form chr1_0000000010_ACTACGACCA (SEQ ID NO: 2) refers to the haplotype ACTACGACCA (SEQ ID NO: 2) observed in the window beginning at the 10th SNP on chromosome 1. Executing a "Get" operation against the Window Match table with this key returns a list of all users having that haplotype at that position, which could be, for example, the following collection of columns:

$U_1$, $U_5$, $U_7$.

This indicates that samples $U_1$, $U_5$, and $U_7$ have at least one copy of that haplotype in this window on this chromosome. Word identification module 103 adds a new row to table 202 each time a haplotype is observed for a first time at a particular window on a particular chromosome, and adds an indicator to each user's column if that user's sample includes the presence of that haplotype.

Referring now to FIG. 3, word identification module 103 also populates a haplotype table 302 with the raw phased haplotype data for each window and each sample. The row keys for haplotype table 302 are of the form [CHROMOSOME] [USER ID]. The columns in haplotype table 302 represent the pair of haplotypes observed in each window for the specified sample and chromosome. Each column is indexed by [POSITION] [EVEN OR ODD]. In the illustrated embodiment, the position is the first base in that particular window as numbered from the beginning of the sequence of nucleic acids for that sample. The value for each cell is the sequence for the specified sample at the given chromosome and position. When populating the table with new data, word identification module 103 arbitrarily labels each chromosomal haplotype pair as ODD or EVEN, thus while these definitions are consistent between neighboring windows on the same chromosome, there is no relationship between different chromosomes of the same individual. In the example illustrated in FIG. 3, the row key is of the form Chr1_$U_1$. This key would return all haplotype data for each window for sample $U_1$ on chromosome 1. Storing the sequence of each window is useful for fuzzy matches between individuals after exact matches have been determined, as described further below. Word identification module 103 in the illustrated embodiment continues to add rows for each user and each chromosome until all of the initial samples are reflected in haplotypes table 302.

Next, and referring now to FIG. 4, matching module 105 populates the segment match table 402 to identify individuals who have at least one haplotype in common at a given location. Matching module 105 uses data from the word match table 202 as well as the haplotype table 302. These pairs of individuals are stored in the segment match database 109. The operation of the matching module 105 is discussed in greater detail below.

FIG. 4 illustrates a segment match table 402 according to one embodiment. Each row index represents a specific user and chromosome combination. Each column represents an individual and each cell contains a coordinate array indicating the locations of matching segments on that chromosome between the specified pair of individuals. In various embodiments, only matching segments of at least a threshold length, e.g., 5 Mb, 1 cM, etc., as determined by the implementer, are considered a match for purposes of insertion into table 402. The row key for this table in the illustrated embodiment is of the form [CHROMOSOME] [USER ID]. In the first row of FIG. 4, the row key Chr1_$U_1$ specifies the row containing matches for user 1 along chromosome 1. Performing a "Get" operation against the segment match table 402 with key Chr1_$U_1$ returns column $U_2$ for user 2 as well as other users with whom user 1 has segments in common. For example, the operation might return:

$U_2$, $U_4$, $U_{538}$, $U_{7034}$, indicating that the sample with ID $U_1$ has segments in common with samples $U_2$, $U_4$, $U_{538}$, and $U_{7034}$.

The cell for $U_2$ might contain values 10-40, 120-130, 550-700, 800-4560, indicating that along chromosome 1, for segment ranges 10-40, 120-130, 550-700, 800-4560 samples $U_1$ and $U_2$ contain at least one haplotype that is identical or nearly identical.

Matching module 105 proceeds to populate the segment match table 402 for each user and each chromosome. In one embodiment, a fuzzy matching algorithm is used to extend identified matches between the haplotypes of two users. For example, suppose that within chromosome 1, $U_1$ has an exact segment matching with $U_{532}$ from SNPs 100-299. Matching module 105 executes a fuzzy extension process that attempts to extend this match on both sides while allowing for small numbers of unmatched bases. To extend this segment on the left flank, matching module 105 performs a "Get" call against haplotypes table 302, supplying the row keys chr1_$U_1$ and chr1_$U_{532}$, requesting the following columns:

0000000000_E, 0000000000_O, 0000000010_E, 0000000010_O . . . 0000000090_E, 0000000090_O.

The cells of this table contain the actual haplotypes for these windows and matching module 105 can extend a match by locating the sites containing alternate homozygotes (e.g., T/T for one sample and G/G for the other). Depending on the parameters specified by the implementer, fuzzy match extension proceeds until x alternate homozygotes are encountered. This process is repeated for each flank of each segment, updating the appropriate cells in segment match table 402 to reflect the longer matching string. Matching module 105 proceeds to populate the segment match table 402 for each user and each chromosome.

Addition of New Samples

After the initial population of tables 302, 202 and 402 in their respective databases 111, 107, 109 by word identification module 103 and matching module 105, new samples from additional individuals 101 can be received, and relationships between those individuals and both the previously processed individuals and other new individuals can be determined as described below.

Figure 5:
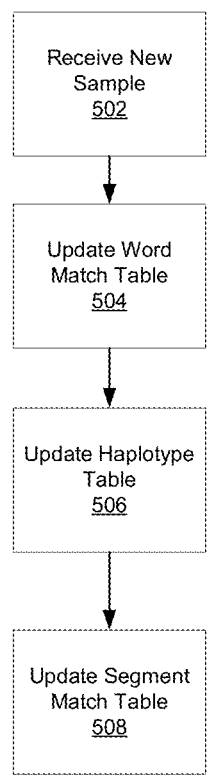
FIG. 5 illustrates a process for processing new samples in accordance with one embodiment.

Referring to FIG. 5, a process for processing new samples can be described generally as follows. A new sample is received 502 and stored in DNA database 113 as described above. Word match table 202 is updated 504, haplotypes table 302 is updated 506, and segment match table 402 is also updated 508 to reflect the newly identified relationships. We describe each of these processes in turn.

Figure 6:
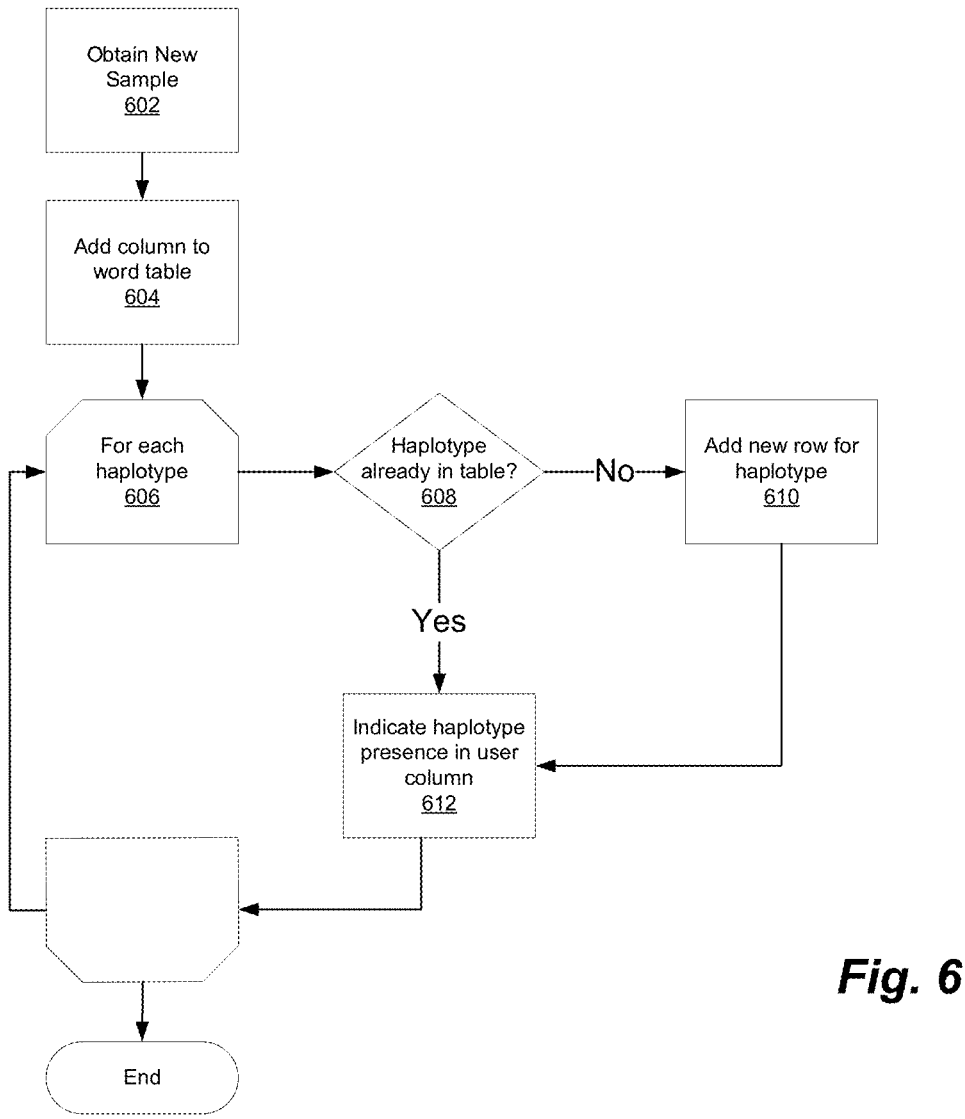
FIG. 6 illustrates a process for updating a word match table in accordance with one embodiment.

Referring to FIG. 6, word identification module 103 obtains 602 the new sample data, e.g., from DNA database 113. Word identification module 103 then updates the word match table 202, which, as noted, is persistently stored in database 107. To update the table 202, word identification module 103 first adds 604 a column to the world table to accommodate values for the new user. Next 606, for each haplotype in the user sample, identification module 103 determines 608 whether that haplotype is already in table 202. If not, module 103 adds 610 a new row for the table. Once the appropriate row is added or found, module 103 updates the user's column to indicate 612 the presence of the haplotype in the user's sample. The process then repeats 606 for each haplotype and for each newly received sample. The updated word match table 202 remains stored in database 107.

Next, word identification module 103 updates 506 haplotypes table 302 by adding a new row for each chromosome of the new user sample, and inserting the relevant haplotype data for each window.

Figure 7:
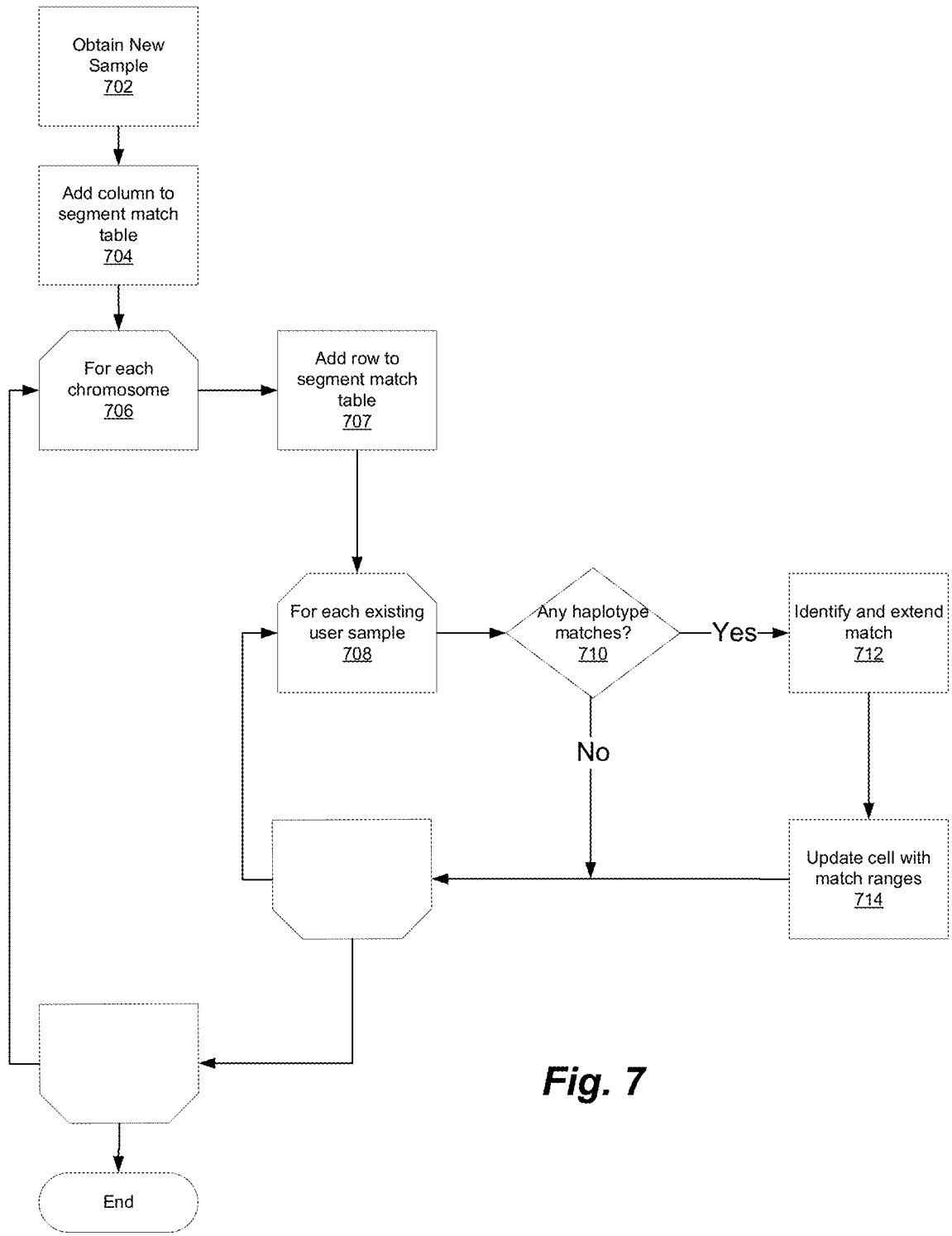
FIG. 7 illustrates a process for updating a segment match table in accordance with one embodiment.

In one embodiment, word identification module 103 updates 504, 506 the word match and haplotypes tables for each new sample being processed in a current batch, and then matching module 105 updates 508 the segment match table 402. Referring to FIG. 7, matching module 105 obtains 702 the new sample data and adds 704 a column to segment match table 402 for the new user. Next 706, for each chromosome of the new user, in an embodiment such as the one illustrated in FIG. 4 in which each row represents a particular chromosome for a particular user, matching module 105 adds 707 a row to segment match table 402. Then 708, for each of the existing users with data in table 402, matching module 105 determines 710 whether any haplotype matches of a minimum threshold length exist between the new user's sample and the existing user's sample on that chromosome. If so, matching module 105 extends 712 the match where possible, using a fuzzy logic approach described above, and enters 714 the results of the match in the appropriate cell of table 402. This process then continues, matching the new user against each existing user across each chromosome.

In one embodiment, following the update procedure of FIG. 5, a reducer is executed that eliminates duplicate matches due to reciprocal comparisons and creates an output file with the results from the process run. The data in the file is then usable to inform the implementer about potential relationships due to IBD between the various user samples. In some embodiments, system 100 is implemented as part of a service that enables subscribing users to submit samples and receive reports about other subscribers to whom they may be related, for example for those users who share a sufficiently high number of haplotype matches as described above. Depending on a user's privacy settings and opt-in preferences, examples of information provided might include blind (anonymous) introductions, account identifiers, or names or other contact information.

In addition to the embodiments specifically described above, those of skill in the art will appreciate that the invention may additionally be practiced in other embodiments. Within this written description, the particular naming of the components, capitalization of terms, the attributes, data structures, or any other programming or structural aspect is not mandatory or significant unless otherwise noted, and the mechanisms that implement the described invention or its features may have different names, formats, or protocols. Further, the system may be implemented via a combination of hardware and software, as described, or entirely in hardware elements. Also, the particular division of functionality between the various system components described here is not mandatory; functions performed by a single module or system component may instead be performed by multiple components, and functions performed by multiple components may instead be performed by a single component. Likewise, the order in which method steps are performed is not mandatory unless otherwise noted or logically required. It should be noted that the process steps and instructions of the present invention could be embodied in software, firmware or hardware, and when embodied in software, could be downloaded to reside on and be operated from different platforms used by real time network operating systems.

Algorithmic descriptions and representations included in this description are understood to be implemented by computer programs. Furthermore, it has also proven convenient at times, to refer to these arrangements of operations as modules or code devices, without loss of generality.

Unless otherwise indicated, discussions utilizing terms such as "selecting" or "computing" or "determining" or the like refer to the action and processes of a computer system, or similar electronic computing device, that manipulates and transforms data represented as physical (electronic) quantities within the computer system memories or registers or other such information storage, transmission or display devices.

The present invention also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, DVDs, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and displays presented are not inherently related to any particular computer or other apparatus. Various general-purpose systems may also be used with programs in accordance with the teachings above, or it may prove convenient to construct more specialized apparatus to perform the required method steps. The required structure for a variety of these systems will appear from the description above. In addition, a variety of programming languages may be used to implement the teachings above.

Finally, it should be noted that the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention.

We claim:

1. A computer-implemented method, comprising:
accessing a new sample of genotype dataset;
accessing three tables storing existing samples of genotype datasets, (1) a first table indexed by haplotype sequence, each haplotype sequence associated with one or more identifiers of existing samples that include the each haplotype sequence, (2) a second table storing a plurality of haplotype sequences that are grouped in rows, each row corresponding to one of the existing samples, and that are sorted by positions in DNA sequence, and (3) a third table identifying sequence matching positions among the existing samples;
updating the third table with the new sample of genotype dataset, the updating the third table comprising:
identifying a particular haplotype sequence of the new sample;
identifying one of the existing samples that has a match of the particular haplotype sequence by accessing the first table, locating an index associated the particular haplotype sequence, and identifying an identifier of the one of the existing samples that is associated with the index;
accessing, based on the identifier, a row of the second table corresponding to the one of the existing sample, the row comprising the particular haplotype sequence and other haplotype sequences, the particular haplotype sequence being flanked by the other haplotype sequences in DNA sequence of the one of the existing samples;
extending the match of the particular haplotype sequence between the new sample and the one of the existing samples along nucleotide bases of the other haplotype sequences stored in the row of the second table;
determining a range of extended matches of haplotype sequences between the new sample and the one of the existing samples; and
adding the range of extended matches as a new entry in the third table.

2. The computer-implemented method of claim 1, wherein the first table comprises a plurality of rows and column, a column comprises different haplotype sequences, each row comprises one of the different haplotype sequences and the one or more identifiers of existing samples that include the one of the different haplotype sequences.

3. The computer-implemented method of claim 1, wherein each row of the second table is identified by a row key, and the row key is one of the identifiers of existing samples.

4. The computer-implemented method of claim 1, wherein the third table comprises a plurality of rows and columns, each row represents a user and each column also represents a user, and a cell of a particular row and a particular column comprises data indicating locations of the sequence matching positions between a first specific user represented by the particular row and a second specific user represented by the particular column.

5. The computer-implemented method of claim 1, wherein identifying one of the existing samples that has the match of the particular haplotype sequence comprises matching segments of haplotypes of at least a threshold length.

6. The computer-implemented method of claim 1, wherein the first table is indexed by hash values of the plurality of haplotype sequences.

7. The computer-implemented method of claim 6, further comprising updating the first table, updating the first table comprises:
identifying a specific haplotype sequence in the new sample;
hashing the identified haplotype sequence to generate a hash value of the identified haplotype sequence;
identifying the hash value of the identified haplotype sequence in the first table; and
associated an identifier of the new sample with the hash value in the first table.

8. The computer-implemented method of claim 1, further comprising updating the first table by associating an identifier of the new sample to each haplotype sequences included in the new sample.

9. The computer-implemented method of claim 1, further comprising updating the second table by adding a new row using an identifier of the new sample, the new row including haplotype sequences included in the new sample that are sorted by positions in DNA sequence.

10. The computer-implemented method of claim 1, wherein the range of extended matches of haplotype sequences comprises a plurality of haplotype values that are sequential in position within or between genomic windows.

11. A non-transitory computer readable medium comprising instructions, when executed by one or more processors, cause the one or more processors to execute steps comprising:
   accessing a new sample of genotype dataset;
   accessing three tables storing existing samples of genotype datasets, (1) a first table indexed by haplotype sequence, each haplotype sequence associated with one or more identifiers of existing samples that include the each haplotype sequence, (2) a second table storing a plurality of haplotype sequences that are grouped in rows, each row corresponding to one of the existing samples, and that are sorted by positions in DNA sequence, and (3) a third table identifying sequence matching positions among the existing samples;
   updating the third table with the new sample of genotype dataset, the updating the third table comprising:
      identifying a particular haplotype sequence of the new sample;
      identifying one of the existing samples that has a match of the particular haplotype sequence by accessing the first table, locating an index associated the particular haplotype sequence, and identifying an identifier of the one of the existing samples that is associated with the index;
      accessing, based on the identifier, a row of the second table corresponding to the one of the existing sample, the row comprising the particular haplotype sequence and other haplotype sequences, the particular haplotype sequence being flanked by the other haplotype sequences in DNA sequence of the one of the existing samples;
      extending the match of the particular haplotype sequence between the new sample and the one of the existing samples along nucleotide bases of the other haplotype sequences stored in the row of the second table;
      determining a range of extended matches of haplotype sequences between the new sample and the one of the existing samples; and
      adding the range of extended matches as a new entry in the third table.

12. The non-transitory computer readable medium of claim 11, wherein the first table comprises a plurality of rows and column, a column comprises different haplotype sequences, each row comprises one of the different haplotype sequences and the one or more identifiers of existing samples that include the one of the different haplotype sequences.

13. The non-transitory computer readable medium of claim 11, wherein each row of the second table is identified by a row key, and the row key is one of the identifiers of existing samples.

14. The non-transitory computer readable medium of claim 11, wherein the third table comprises a plurality of rows and columns, each row represents a user and each column also represents a user, and a cell of a particular row and a particular column comprises data indicating locations of the sequence matching positions between a first specific user represented by the particular row and a second specific user represented by the particular column.

15. The non-transitory computer readable medium of claim 11, wherein identifying one of the existing samples that has the match of the particular haplotype sequence comprises matching segments of haplotypes of at least a threshold length.

16. The non-transitory computer readable medium of claim 11, wherein the first table is indexed by hash values of the plurality of haplotype sequences.

17. The non-transitory computer readable medium of claim 16, wherein the steps further comprises updating the first table, updating the first table comprises:
   identifying a specific haplotype sequence in the new sample;
   hashing the identified haplotype sequence to generate a hash value of the identified haplotype sequence;
   identifying the hash value of the identified haplotype sequence in the first table; and
   associated an identifier of the new sample with the hash value in the first table.

18. The non-transitory computer readable medium of claim 11, wherein the steps further comprises updating the first table by associating an identifier of the new sample to each haplotype sequences included in the new sample.

19. The non-transitory computer readable medium of claim 11, wherein the steps further comprises updating the second table by adding a new row using an identifier of the new sample, the new row including haplotype sequences included in the new sample that are sorted by positions in DNA sequence.

20. The non-transitory computer readable medium of claim 11, wherein the range of extended matches of haplotype sequences comprises a plurality of haplotype values that are sequential in position within or between genomic windows.

* * * * *

SEQUENCE LISTING

```
<160> NUMBER OF SEQ ID NOS: 7

<210> SEQ ID NO 1
<211> LENGTH: 10
<212> TYPE: DNA
<213> ORGANISM: Homo sapiens

<400> SEQUENCE: 1
gccatatggc                                                          10

<210> SEQ ID NO 2
<211> LENGTH: 10
<212> TYPE: DNA
<213> ORGANISM: Homo sapiens

<400> SEQUENCE: 2
actacgacca                                                          10

<210> SEQ ID NO 3
<211> LENGTH: 10
<212> TYPE: DNA
<213> ORGANISM: Homo sapiens

<400> SEQUENCE: 3
actacgactc                                                          10

<210> SEQ ID NO 4
<211> LENGTH: 10
<212> TYPE: DNA
<213> ORGANISM: Homo sapiens

<400> SEQUENCE: 4
tcgccttagc                                                          10

<210> SEQ ID NO 5
<211> LENGTH: 10
<212> TYPE: DNA
<213> ORGANISM: Homo sapiens
```

```
<400> SEQUENCE: 5
ttcgctaaca                                                            10

<210> SEQ ID NO 6
<211> LENGTH: 10
<212> TYPE: DNA
<213> ORGANISM: Homo sapiens

<400> SEQUENCE: 6
tcgcctgaga                                                            10

<210> SEQ ID NO 7
<211> LENGTH: 10
<212> TYPE: DNA
<213> ORGANISM: Homo sapiens

<400> SEQUENCE: 7
actacgaccc                                                            10
```